United States Patent [19]

Baudin

[11] Patent Number: 5,332,725
[45] Date of Patent: Jul. 26, 1994

[54] ODORANTS

[75] Inventor: Josianne Baudin, Annemasse, France

[73] Assignee: Givaudan-Roure Corporation, Clifton, N.J.

[21] Appl. No.: 135,146

[22] Filed: Oct. 12, 1993

[51] Int. Cl.$^5$ .................. A61K 7/46; C07C 43/168
[52] U.S. Cl. ............................ 512/14; 512/17; 568/659; 568/327; 568/44
[58] Field of Search .............. 568/659, 327, 440; 512/14, 17

[56] References Cited

U.S. PATENT DOCUMENTS

| | | | |
|---|---|---|---|
| 4,250,200 | 2/1981 | Wiegers et al. | 252/522 R |
| 4,650,603 | 3/1987 | Sprecker | 426/536 |
| 5,084,440 | 1/1992 | Baudin et al. | 512/12 |

FOREIGN PATENT DOCUMENTS 0379981 8/1990 European Pat. Off. .

OTHER PUBLICATIONS

Theimer, "Fragrance Chemistry, The Science of Smell" (1982), pp. 514–529.

*Primary Examiner*—Howard T. Mars
*Assistant Examiner*—Margaret J. Page
*Attorney, Agent, or Firm*—George M. Gould; George W. Johnston

[57] ABSTRACT

The invention is concerned with novel odorants, namely enol ethers of alky-substituted oxo-tetralins and oxo-indanes, for example of oxo-tetralins or oxo-indanes having up to 6 or 7 alkyl substituents.

15 Claims, No Drawings

ODORANTS

The invention relates to novel odorants, namely enol ethers of alkyl-substituted oxo-tetralins and oxo-indanes, for example of oxo-tetralins and oxo-indanes having up to 6 or 7 alkyl substituents.

In particular, the invention is concerned with the compounds of the formula

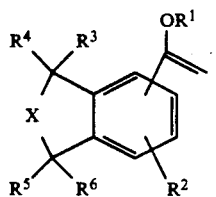

wherein
$R^1$ is $C_{1-4}$ alkyl or $C_{2-4}$ alkenyl
$R^2$ signifies H or $C_{1-4}$ alkyl
$R^3$, $R^4$, $R^5$ and $R^6$ each independently signify H, $CH_3$, $C_2H_5$, $CH_2-CH_2-CH_3$ or $CH(CH_3)_2$,
X is methylene, ethylidene, propylidene, ethylene, propylene, isopropylidene or 1,2-dimethyl-ethylene,
and the total number of carbon atoms of $R^3$, $R^4$, $R^5$ and $R^6$ is $\leq 6$.

The compounds of formula I are distinguished by very natural notes in the direction of musk, woody, sweet, fruity and floral.

In contrast to the corresponding ketals II, an important technical advantage in the use of the enol ethers I results from the fact that they furnish liquid mixtures when blended with one or more Polycyclic Musks, See e.g., Ernst T. Theimer in "Fragrance Chemistry, The Science of the Sense of Smell", pages 514 to 528 (1982), which describes such Polycyclic Musks (e.g. Fixolide, Crysolide, Phantolide, Novalide, Galaxolide, etc.). A preferred execution is the blending with the parent carbonyl compounds III which are described below.

Thus, it is possible by mixing the novel compounds I and known musk odorants, i.e. the corresponding basic carbonyl compounds III, such as Fixolide, Phantolide, Crysolide etc. to manufacture liquid musks of variable intensity. These mixtures are generally sweeter (generally with a fruity side note), better balanced and more natural than the Polycyclic Musks as such.

The optimal ratio of compounds I/Polycyclic Musks is in each case based on economic reasons according to the intended utilization (e.g. alcoholic perfumery or the perfuming of laundry, etc.) and of the desired fluidity of the mixtures obtained; this pronounced and varying fluidity of the mixtures of the carbonyl compounds III/enol ethers I being a further technical advantage. The ratio lies, for example, between about 1:10 to about 1: For economic reasons a smaller proportion of the more expensive enol ether will typically be desirable.

The compounds I may be obtained by the elimination of an equivalent of the alcohol $R^1OH$ from the ketal

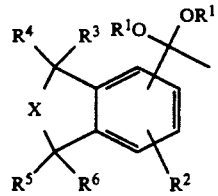

conveniently in the usual manner, expediently at elevated temperatures and acid-catalyzed.

Suitable acids are mineral acids, such as HCl, $H_3PO_4$, $H_2SO_4$, or $H_3BO_3$, acidic salts such as $KHSO_4$, organic acids such as p-toluene sulphonic acid, acidic ion exchangers, e.g. of the Amberlyst 15 type.

A suitable temperature range is preferably between about 40° C. and 120° C., more preferably between about 60° C. and about 80° C.

Solvents are optional, and are preferably selected from the group of alkanols and aliphatic or aromatic hydrocarbons.

The isolation is preferably effected by distillation under reduced pressure and column chromatography.

In case of the novel mixtures of carbonyls III and enol ethers I mentioned above, it is convenient to prepare the enol ethers I from the compounds II prepared in situ.

According to EP-A$_1$ 379 981, which is incorporated herein by reference, the ketals II can be manufactured by reacting the basic ketone, i.e. the compound of formula

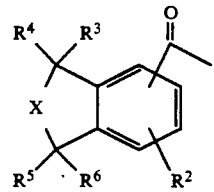

with an excess, e.g. a two fold excess, of ortho formic esters in alcohols, and especially at temperatures between about 20° to about 40° C.

Scaling down the amount of ortho formic ester to below, say equimolar amounts, for example, and raising the temperature above about 40° C., e.g. up to a maximum of about 120° C., leads directly to any desired mixtures of the ketones III and enol ethers I, because the ketal formed initially is this way immediately transferred to the compound I, thus leaving the "basic" ketone III and novel compound I in the reaction vessel.

The parameters of this reaction are analogous to those already described above.

The novel products of this invention (compounds I, compound I+Polycyclic Musks) combine with numerous known odorant ingredients of natural or synthetic origin, whereby the range of the natural raw substances can embrace not only readily-volatile, but also moderately-volatile and slightly-volatile components and that of the synthetics can embrace representatives from practically all classes of substances, as will be evident from the following compilation:

natural products, such as tree moss absolute, basil oil, citrus fruit oils (such as bergamot oil, mandarin oil, etc.), mastix absolute, myrtle oil, palmarosa oil, patchouli oil, petitgrain oil Paraguay, wormwood oil, alcohols, such as farnesol, geraniol, linalool, nerol, phenylethyl alcohol, rhodinol, cinnamic alcohol, aldehydes, such as citral, Helional ®, α-hexyl-cinnamaldehyde, hydroxycitronellal, Lilial ® (p-tert-.butyl-α-methyldihydrocinnamal-dehyde), methylnonylacetaldehyde, ketones, such as allylionone, α-ionone, β-ionone, isoraldein (isomethyl-α-ionone), methylionone, esters, such as allyl phenoxyacetate, benzyl salicylate, cinnamyl propionate, citronellyl acetate, citronellyl ethoxolate (citronellyl.O—CO—CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linaly; acetate, methyl dihydrojasmonate, styrallyl acetate, vetiveryl acetate, etc., lactones, such as γ-undecalactone, various components often used in perfumery, such as musk ketone, indole, p-menthane-8-thiol-3-one, methyl-eugenol.

The novel products can be used in wide limits which can range in compositions, for example, from about 0.1 (detergents) to about 20% by weight (alcoholic solutions), without these values being, however, limiting values, as the experienced perfumer can also achieve effects with even lower concentrations or can synthesize novel complexes (i.e. compositions) with even higher amounts. The preferred concentrations range between about 1% and about 10%.by weight. The compositions manufactured with I can be used for all kinds of perfumed consumer goods (eau de cologne, eau de toilette, extracts, lotions, creams, shampoos, soaps, salves, powders, toothpastes, mouthwashes, deodorants, detergents, fabric conditioners, tobacco, etc.).

The products can accordingly be used in the manufacture of compositions and—as the above compilation shows—using a wide range of known odorants or odorant mixtures. In the manufacture of such compositions the known odorants referred to above can be used according to methods known to the perfumer. See W. A. Poucher, "Perfumes, Cosmetics and Soaps", 2, 7th Edition, Chapman and Hall, London, 1974, which is incorporated herein by reference.

EXAMPLES

General methology

A mixture of the appropriate ketal e.g. (0.6 mol) in 200 ml of toluene was treated with 0.5 g of p-toluene sulfonic acid and was boiled in a round-bottomed flask equipped with a Hahn head (a dephlegmator device) and a vertical condenser. The alcohol R1OH of the particular ketal was used as the cooling liquid in the Hahn head. The alcohol formed slowly in the reaction distilled off and was collected in a measuring cylinder so that the progress of the reaction could easily be followed. After the alcohol had been eliminated, the reaction mass was neutralized by the addition of a 10% solution of potassium hydroxide in ethanol and the solvent was evaporated under reduced pressure. The pure enol ether was thus obtained by distillation under vacuum.

EXAMPLE 1

The following enol ethers were prepared from the corresponding ketals according to the method outlined above.

a) 6-(1-Ethoxy-vinyl)-1,1,4,4-tetramethyl-tetralin

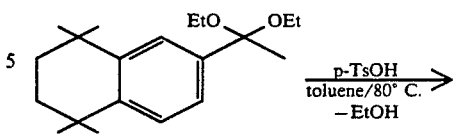

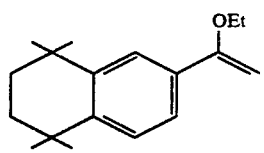

The distillation under vacuum of the crude product provided a colorless liquid enol ether which contained about 10% of the carbonyl compound III; bp: 150° C. (2 mbar).

GC: column 30 meters×0.53 ram, Carbowax stationary phase (Supelcowax) programmed at 120°-220° C. at 5° C. per minute.

$^1$H-NMR (200 MHz; CDCl$_3$): 1.27 (s,6H); 1.29 (s,6H), 1.42 (t,J=7 Hz,3H); 1.68 (s,4H); 3.91 (q,J=7 Hz,2H), 4.14 (d,J=2 Hz,1H); 4.57 (d,J=2 Hz,1H); 7.24 at 7.40 (m,2H); 7.56 (d,J=2 Hz, 1H); δ=ppm.

MS: 258 (43,M$^+$), 243(61), 215(100), 197(34), 155(30), 57(21), 43(90).

b) 6-(1-Methoxy-vinyl)-1,1,2,4,4,7-hexamethyl-tetralin

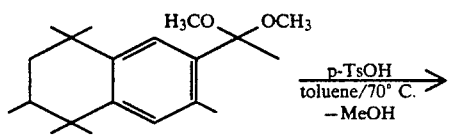

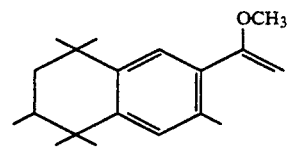

After the distillation of the reaction mass, the product was purified by flash chromatography on silicagel with hexane/diethyl ether 40:1 as eluent. Purity 100% by GC (Supelcowax), mp: 40.2°–41.6° C.

$^1$H-NMR (200 MHz; CDCl$_3$): 0.98 (d,J=7 Hz,3H); 1.04 (s,3H), 1.24 (s,3H); 1.28 (s, 3H); 1.30 (s,3H); 1.36 at 1.98 (m,3H); 2.28 (s,3H), 3.68 (s,3H); 4.19 (d,J=2 Hz, 1H); 4.28 (d,J=2 Hz, 1H); 7.14 (s,1H); 7.22 (s,1H); δ=ppm.

MS: 272 (52,M$^{30}$), 257(100), 201(17), 183(33), 169(15), 57(18).

IR: 3120, 3020, 2965, 2930, 2880, 1645, 1610, 1270, 1245, 1190, 1120, 1050, 800 cm$^{-1}$.

Odor: musky, sweet, flowery.

c) 6-(1-Ethoxy-vinyl)-1,1,2,4,4,7-hexamethyl-tetralin

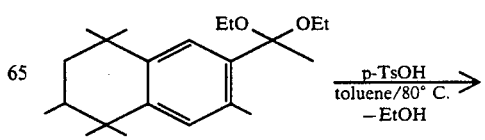

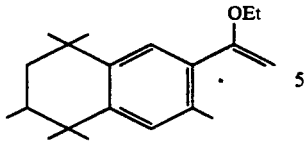

The crude oil was fractionally distilled to yield the pure enol ether (60% yield) purity 98% by GC (Supelcowax), bp: 123° C. (1 mbar), solid white product, mp: 43,2°–44,8° C.

$^1$H-NMR (200 MHz; CDCl$_3$): 0.96 (d,J=7 Hz,3H); 1.05 (s,3H); 1.24 (s,3H); 1.29 (s,3H); 1.31 (s,3H); 1.36 (t,J=7 Hz,3H); 1.42 at 1.96 (m,3H); 2.31 (s,3H); 3.87 (q,J=7 Hz,2H); 4.17 (d,J=2 Hz, 1H); 4.25 (d,J=2 Hz, 1H); 7.13 (s,1H); 7.24 (s,1H); δ=ppm.

MS: 286 (56,M+), 271(80), 257(29), 243(39), 227(100), 201(28), 183(41), 161(34), 57(24), 43(78).

IR: 3120, 3020, 2965, 2930, 2880, 1640, 1600, 1245, 1120, 1060, 800 cm$^{-1}$.

Odor: fruity, sweet, musky, woody.

d) 4-(1-Ethoxy-vinyl)-1,1-dimethyl-6-tert-butyl-indan

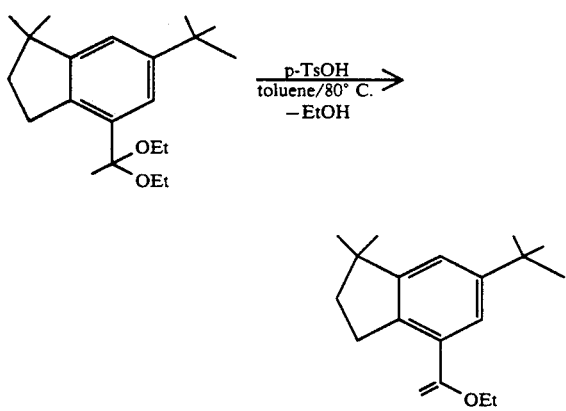

The pure product (95% by GC: Supelcowax) was obtained by distillation under vacuum; Colorless liquid: bp 93° C. (0.8 mbar).

$^1$H-NMR (200 MHz; CDCl$_3$): 1.25 (s,6H); 1.33 (s,9H); 1.40 (t,J=7 Hz,3H); 1.88 (t,J=7 Hz,2H); 2.95 (t,J=7 Hz,2H); 3.88 (q,J=7 Hz,2H); 4.25 (d,J=2 Hz, 1H); 4.32 (d,J=2 Hz,1H); 7.13 (d,J=2 Hz, 1H); 7.33 (d,J=2 Hz, b 1H); δ=ppm.

MS: 272 (46,M+), 257(20), 243(42), 229(30), 213(20), 187(48), 57(54), 43(100).

IR: (pur) 3120, 3060, 2950, 2860, 1645, 1610, 1270, 1245, 1060, 800 cm$^{-1}$.

Odor: musky, fruity, woody.

e) 5-(1-Methoxy-vinyl)-1,1,2,3,3,6-hexamethyl-indan

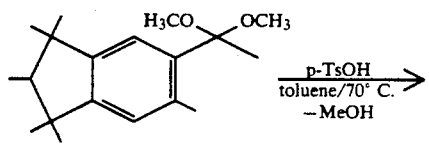

The enol ether was separated from the crude reaction mixture by distillation under vacuum (105° C./2 mbar) and was purified by flash chromatography on silicagel with a mixture hexane/diethylether 50:1 as eluent. Purity 98% by GC (Supelcowax). White solid mp 27.9°–31.4° C.

$^1$H-NMR (200 MHz; CDCl$_3$): 0.98 (d,J=7 Hz,3H); 1.05 (s,6H); 1.26 (s,6H); 1.84 (q,J=7 Hz, 1H); 2.32 (s,3H); 3.69 (s,3H); 4.20 (d,J=2 Hz, 1H); 4.30 (d,J=2 Hz, 1H); 6.95 (s,1H); 7.09 (s,1H); δ=ppm.

MS: 258 (44,M+), 243(100), 211(30), 188(21), 169(12), 57(12), 43(8).

IR: (pur) 3120, 3010, 2960, 2865, 1650, 1610, 1270, 1280, 1130, 1050, 800 cm$^{-1}$.

Odor: musky, slightly fruity.

f) 5-(1-Ethoxy-vinyl)-1,1,2,3,3,6-hexamethyl-indan

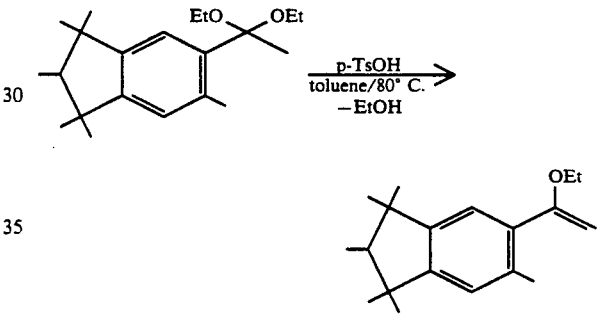

A flash chromatography on silicagel with hexane/diethyl ether 50:1 as eluent of the distilled enol ether (110° C./2 mbar) afforded a pure liquid product. Purity 93% by GC (Supelcowax). Colorless liquid. bp: 110° C. (2 mbar).

$^1$H-NMR (200 MHz; CDCl$_3$): 0.98 (d,J=7 Hz,3H); 1.05 (s,6H); 1.24 (s,6H); 1.36 (q,J=7 Hz,3H); 1.84 (q,J=7 Hz, 1H); 2.33 (s,3H); 3.88 (q,J=7 Hz,2H); 4.17 (d,J=2 Hz, 1H); 4.27 (d,J=2 Hz, 1H); 6.95 (s, 1H); 7.09 (s, 1H); δ=ppm.

MS: 272 (56,M+), 257(89), 243(37), 229(24), 213(100), 202(72), 57(16), 43(49), 29(18).

IR: (pur) 3120, 3000, 2960, 2870, 1640, 1600, 1285, 1270, 1120, 1110, 1060, 800 cm$^{-1}$.

Odor: musky, slightly fruity.

EXAMPLE 2

Preparation of single phase liquid mixtures of enol ethers I and carbonyl compounds III As mentioned above, the liquid mixtures, enol ethers and carbonyl compounds can be directly prepared by reacting ketones and ortho formic esters (e.g. ethyl or methyl ester) in acidic medium without isolating, i.e. extracting, the intermediate ketals.

It is sufficient to adjust the dosage of the starting materials to the desired mixture carbonyl/ether and to remove the formic ester (e.g. ethyl or methyl) and the alcohol (e.g. MeOH or EtOH) formed during the partial acetalyzation and then during the elimination reaction (one mole of alcohol from the ketal). The appropriate liquid mixtures are then conveniently flash distilled under vacuum.

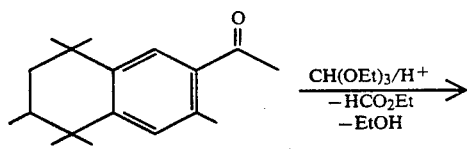

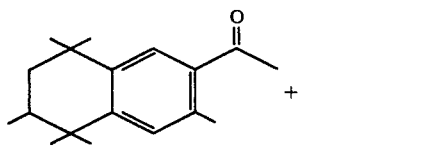

75% +

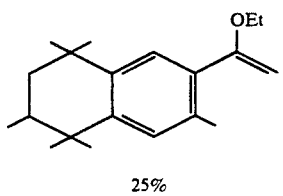

25%

0.4 ml of acetyl chloride were added dropwise within approximately 5 minutes to a mixture of 6 g (0.04 mol) of orthoformic ethyl ester, 4 ml of EtOH and 25.8 g of 6-acetyl-1,1,2,4,4,7-hexamethyl-tetralin (0.1 mol). The reaction mixture was heated at 40° C. for 15 minutes until about 30% of acetal was formed. The reaction was monitored by GC. The reaction mass was then heated at 110° C. and the ethyl formate and ethanol formed were distilled off. After the alcohol had been eliminated, the reaction mass was neutralized by adding a 10% solution of potassium hydroxide in ethanol. A flash distillation under reduced pressure (125° C./2 mbar) yielded 22 g of a colorless liquid mixture containing 25% (GC) of 6-(1-ethoxy-vinyl)-1,1,2,4,4,7-hexamethyl-tetralin and 75% of 6-acetyl-1,1,2,4,4,7-hexamethyl-tetralin.

$^1$H-NMR (200 MHz; CDCl$_3$): 2.31 (s,0.66H); 2.48 (s,2.35H); 2.57 (s,2.32H); 3.87 (q,J=7 Hz,0.36H); 4.17 (d,J=2 Hz,0.22H); 4.25 (d,J=2 Hz,0.22H); 7.13 (s,0.22H); 7.20 (s,0.74H); 7.24 (s,0.22H); 7.66 (s,0.73H).

Odor: musky, fruity.

EXAMPLE 3

| a) Composition for cosmetic consumer goods | Parts per weight |
|---|---|
| Compound of Example 1c) | 150.00 |
| Benzyl acetate | 70.00 |
| Vetivenyl acetate | 40.00 |
| Phenyl ethyl alcohol | 150.00 |
| Hexyl cinnamic aldehyde | 100.00 |
| C 10 aldehyde | 2.00 |
| C 11 aldehyde | 1.00 |
| Methyl anthranilate | 1.00 |
| Bergamotte essence | 150.00 |
| Eugenol | 15.00 |
| Gardenol (methyl phenyl carbinyl acetate) | 5.00 |
| Indolene (8,8$^{bis}$-(3H-indol-3-yl)-2,6-dimethyl-2-octanol) | 2.00 |
| Isoeugenol | 3.00 |
| Isoraldeine 70 (mixture of alpha- and beta-methylionone) | 40.00 |
| Linalool | 50.00 |
| Methyl cedryl cetone | 80.00 |
| Musk ketone (5-t-butyl-1,2,3-trimethyl-4,6-dinitrobenzene) | 10.00 |

| a) Composition for cosmetic consumer goods -continued | Parts per weight |
|---|---|
| Nonadyl (6,8-dimethyl-2-nonanol) | 30.00 |
| Peche pure (γ-undecalactone) | 1.00 |
| Benzyl salicylate | 50.00 |
| 3-cis-Hexenyl salicylate | 30.00 |
| Sandalore (3-methyl-5-(2,2,3-trimethylcyclopent- | 20.00 |
| Total: | 1000.00 |

The addition of the novel enol ether (a powerful fixative) exalted the warm musky and animalic notes and brang a velvety aspect to the composition. The composition received much more volume.

| b) Eau de toilette for women | Parts per weight |
|---|---|
| Compound of Example 1c) | 150.00 |
| Benzyl acetate | 80.00 |
| Phenyl ethyl alcohol | 120.00 |
| Hexyl cinnamic aldehyde | 160.00 |
| C 11 aldehyde 1%/carbitol | 2.00 |
| Phenyl acetic aldehyde | 2.00 |
| Bergamotte essence | 70.00 |
| Cedar wood ess. Virgin. | 50.00 |
| Evernyl (2,4-dimethyl-3,6-dihydroxy dimethyl benzoate) | 3.00 |
| Geraniol pur | 60.00 |
| Clove bud oil | 8.00 |
| Hedione (methyldihydrojasmonate) | 80.00 |
| Heliotropine crist. | 5.00 |
| Hydroxycitronellal | 120.00 |
| Isoraldeine 95 (mixture of alpha- and beta-methylionone) | 30.00 |
| Mandarine ess. | 15.00 |
| Benzyl salicylate | 50.00 |
| 3-cis Hexenyle salicylate | 10.00 |
| Tropional (trans-3-(3,4-methylendioxyphenyl)-2-methyl-propanol) | 15.00 |
| Total: | 1000.00 |

The addition of the novel enol ether confered to the composition an elegant musky note accompanied by a warm and sweet red fruit-like undertone. This addition to a round, well balanced and rich Eau de toilette.

The novel enol ether is a good fixative, it brings about volume and richness, two aspects which are appreciated not only in the top notes but throughout the entire evaporation of the resulting perfume.

I claim:

1. Compounds of the general formula

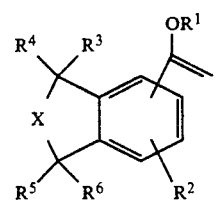

wherein
R$^1$ is C$_{1-4}$ alkyl or C$_{2-4}$ alkenyl
R$^2$ signifies H or C$_{1-4}$ alkyl
R$^3$, R$^4$, R$^5$ and R$^6$ each independently signify H, CH$_3$, C$_2$H$_5$, CH$_2$—CH$_2$—CH$_3$ or CH(CH$_3$)$_2$,
X is methylene, ethylidene, propylidene, ethylene, propylene, isopropylidene or 1,2-dimethylethylene, and the total number of carbon atoms of $R^3$, $R^4$, $R^5$ and $R^6$ is $\leq 6$.

2. The compounds of claim 1, wherein X is methylene.

3. The compounds of claim 1, wherein X is ethylidene.

4. The compounds of claim 1, wherein X is propylidene.

5. The compounds of claim 1, wherein X is ethylene.

6. The compounds of claim 1, wherein X is propylene.

7. The compounds of claim 1, wherein X is isopropylidene.

8. The compounds of claim 1, wherein X is 1,2-dimethylethylene.

9. The compound of claim 2, which is 4-(1-Ethoxyvinyl)-1, 1-dimethyl-6-tert-butyl-indan.

10. The compound of claim 3, which is 5-(1-Methoxyvinyl)-1, 1, 2, 3, 3, 6-hexamethyl-indan.

11. The compound of claim 3, which is 5-(1-Ethoxyvinyl)-1, 1, 2, 3, 3, 6-hexamethyl-indan.

12. The compound of claim 5, which is 6-(1-Ethoxyvinyl)-1, 1, 4, 4-tetramethyl-tetralin.

13. The compound of claim 6, which is 6-(1-Methoxyvinyl)-1, 1, 2, 4, 4, 7-hexamethyl-tetralin.

14. The compound of claim 6, which is 6-(1-Ethoxyvinyl-)-1, 1, 2, 4, 4, 7-hexamethyl-tetralin.

15. An odorant composition, comprising a compound I of claim 1.

* * * * *

UNITED STATES PATENT AND TRADEMARK OFFICE
CERTIFICATE OF CORRECTION

PATENT NO. : 5,332,725
DATED : July 26, 1994
INVENTOR(S): Josianne Baudin

It is certified that error appears in the above-identified patent and that said Letters Patent is hereby corrected as shown below: Title page:

Item [30]: Foreign Application Priority Data

Oct.26,1992 [EP] European 92810824.0

Signed and Sealed this

Thirteenth Day of December, 1994

Attest:

BRUCE LEHMAN

*Attesting Officer*   *Commissioner of Patents and Trademarks*